(12) United States Patent
Bartley et al.

(10) Patent No.: US 7,553,696 B2
(45) Date of Patent: Jun. 30, 2009

(54) METHOD FOR IMPLEMENTING COMPONENT PLACEMENT SUSPENDED WITHIN GRID ARRAY PACKAGES FOR ENHANCED ELECTRICAL PERFORMANCE

(75) Inventors: Gerald Keith Bartley, Rochester, MN (US); Darryl John Becker, Rochester, MN (US); Paul Eric Dahlen, Rochester, MN (US); Philip Raymond Germann, Oronoco, MN (US); Andrew Benson Maki, Rochester, MN (US); Mark Owen Maxson, Mantorville, MN (US)

(73) Assignee: International Business Machines Corporation, Armonk, NY (US)

( * ) Notice: Subject to any disclaimer, the term of this patent is extended or adjusted under 35 U.S.C. 154(b) by 325 days.

(21) Appl. No.: 11/467,952

(22) Filed: Aug. 29, 2006

(65) Prior Publication Data

US 2008/0054453 A1    Mar. 6, 2008

(51) Int. Cl.
*H01L 21/00* (2006.01)
*H01L 23/48* (2006.01)
*H01R 43/00* (2006.01)

(52) U.S. Cl. .................... 438/107; 438/109; 29/857; 257/772

(58) Field of Classification Search .................. None
See application file for complete search history.

(56) References Cited

U.S. PATENT DOCUMENTS 4,734,818 A * 3/1988 Hernandez et al. ....... 361/306.2
6,320,249 B1 * 11/2001 Yoon .......................... 257/678

* cited by examiner

*Primary Examiner*—Alonzo Chambliss
(74) *Attorney, Agent, or Firm*—Joan Pennington

(57) ABSTRACT

A method and structure are provided for implementing component placement suspended within electrical pin grid array packages for enhanced electrical performance. A solder column grid array is coupled between a printed circuit board and a first level package. A component is connected between a predefined pair of adjacent columns in the solder column grid array suspended between the printed circuit board and the first level package.

7 Claims, 5 Drawing Sheets

METHOD FOR IMPLEMENTING COMPONENT PLACEMENT SUSPENDED WITHIN GRID ARRAY PACKAGES FOR ENHANCED ELECTRICAL PERFORMANCE

FIELD OF THE INVENTION

The present invention relates generally to the data processing field, and more particularly, relates to a method and structure for implementing component placement suspended within electrical pin grid array packages for enhanced electrical performance.

DESCRIPTION OF THE RELATED ART

Current and future high performance computer systems and server systems rely on both large-scale packaging of multiple high density interconnect modules and printed circuit boards. High signal speed integrated circuit devices are being fabricated in increasingly smaller sizes and requiring increasing numbers of connector pins or other connection interface structures within a spatial footprint.

In electronics systems there are various electronic components that require connection to other electronic components or to other levels of packaging. Examples include mounting of integrated circuit chips to a metalized substrate, multilayer ceramic substrate (MLC), laminate organic substrate, glass ceramic substrate, card (direct-chip-attach, DCA), and any substrate made of composite materials meeting thermal and mechanical properties. A second level surface mount technology, such as, a column grid array (CGA) or a ball grid array (BGA) typically is used to form an interconnection between a circuit board and an electronic module assembly such as a chip connected to a MLC.

A need exists to efficiently and effectively contain more components in a smaller area within electrical pin grid array packages. Effective placement also is needed for components, such as decoupling capacitors and various termination resistors.

A requirement for decoupling capacitance provided by the electrical packaging is a low inductive path to the noise source. Just as important as having a low inductive path to the noise source is the need for the decoupling capacitance to be in the current flow path. Today there are a multitude of approaches being used to incorporate capacitors into an application. Clearly, on-chip charge is the most effective, but this also requires some of the most expensive circuit real-estate available.

A common approach is placing capacitors on the top-surface of the substrate, but due to the distance and the sometimes un-natural current path, this charge can be inefficient. Capacitors placed on the bottom surface of the substrate are effective, but generally force a recess or hole to be created in the adjoining card to accommodate the devices. This hole forces power distribution to generally be at the periphery of the substrate, and thus a longer path is created on the substrate than approaches which do not require a hole to be placed in the card.

Many package designers are solving these problems by attaching surface mount components on the opposite side of the printed circuit board from the package. These capacitors can be effective, and they are also closer, but are still not directly in the current path and have the disadvantage of being in a longer vertical path defined by the thickness of the card, and therefore at a reduced performance.

As used in the following description and claims the terms electrical pin grid array and solder column grid array (CGA) should be understood to include various grid array packages including solder columns and other pins formed of electrically conductive material.

SUMMARY OF THE INVENTION

Principal aspects of the present invention are to provide a method and structure for implementing component placement suspended within electrical pin grid array packages for enhanced electrical performance. Other important aspects of the present invention are to provide such method and structure for implementing component placement suspended within electrical pin grid array packages for enhanced electrical performance substantially without negative effect and that overcome many of the disadvantages of prior art arrangements.

In brief, a method and structure are provided for implementing component placement suspended within electrical pin grid array packages for enhanced electrical performance. A solder column grid array is coupled between a printed circuit board and a first level package. A component is connected between a predefined pair of adjacent columns in the solder column grid array suspended between the printed circuit board and the first level package.

In accordance with features of the invention, the components are electrically connected between adjacent columns using a high temperature solder or braze. Selected components can provide column-to-column termination including power to ground connection for enhanced power decoupling. Selected components can provide column-to-column termination including one signal to another signal, for example, defining a differential pair. Selected components can provide column-to-column termination including one signal to a reference voltage plane, such as a memory termination to reference voltage Vref. The components are arranged for electrical connection within grid array packages to provide enhanced electrical performance.

In accordance with features of the invention, a column attach fixture used to hold the columns of the column grid array prior to attach to the substrate is modified to receive components between selected columns. This modification simply incorporates slots or reliefs in the fixtures to accommodate the selected components, such as capacitors and resistors, between the columns or pins. Pre-tinning, or pre-application of solder or a braze paste or conductive adhesive is provided for the components. Then the components are placed in the fixture to be cured or reflowed in the course of attachment to the printed circuit board or substrate.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In accordance with features of the preferred embodiments, selected components are suspended within a solder column grid array that is used for first level package attach to printed circuit boards. The selected components include, for example, standard surface mount technology (SMT) capacitors, and SMT resistors. Decoupling capacitors are suspended within the solder column grid array of the electrical packaging to have a low inductive path to the noise source and can be effectively located within the current path. On-board termination requirements for resistors that are suspended within the solder column grid array of the electrical packaging, can be optimally placed nearer the receiving circuit, and with respect to on substrate filtering. By allowing the incorporation of resistors, and various small ferrite products, that are suspended within the solder column grid array, on-board termination networks are more effective and smaller than the conventional arrangements, which place these components a larger distance away from the board-to-packaging boundary creating otherwise unneeded stubs, and reduced performance.

Figure 1:
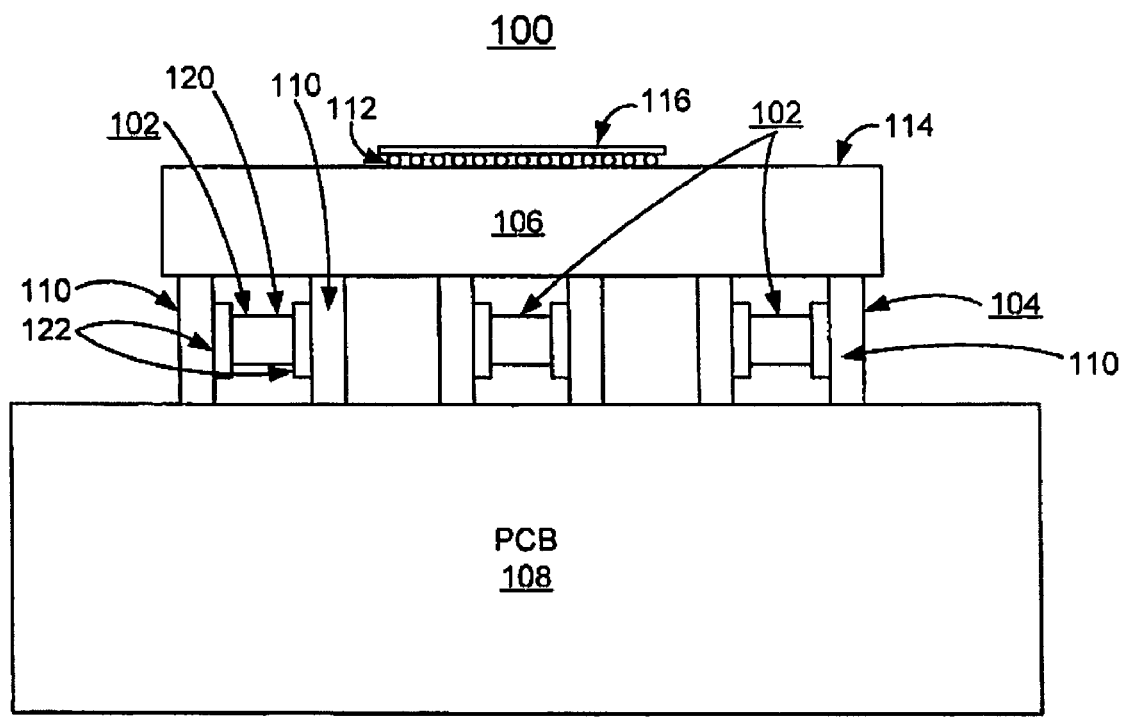
FIG. 1 is a partly schematic and side view not to scale of an electrical pin grid array package assembly with incorporated suspended components in accordance with the preferred embodiment.

Having reference now to the drawings, in FIG. 1, there is shown an electrical pin grid array package assembly generally designated by the reference character 100 with incorporated suspended components 102 in accordance with the preferred embodiment. One or multiple components 102 are suspended within a solder column grid array generally designated by the reference character 104 that is used for attaching a first level package 106 to a printed circuit board (PCB) 108.

Solder column grid array 104 includes a plurality of columns 110 arranged in the grid array. The columns 110 typically are formed of solder. Selected ones of the columns 110 optionally are formed of another electrically conductive material, for example, in forming a subassembly as illustrated and described with respect to FIGS. 4A and 4B.

First level package 106 includes a plurality of electrical connections 112 on the upper surface 114 arranged as, for example, a grid of solder bumps for electrically connecting to, for example, a chip die 116.

As shown, the suspended components 102 include an elongated body portion 120 extending between opposing enlarged ends 122. The opposing enlarged ends 122 are formed of an electrically conductive material, such as a selected metal, for electrically connecting to associated solder columns 110. The suspended components 102 define, for example, standard surface mount technology (SMT) capacitors, or SMT resistors.

Selected suspended components 102, such as coupling capacitors provide column-to-column termination including power to ground connection for enhanced power decoupling.

Selected suspended components 102, such as termination resistors, provide column-to-column termination including one signal to another signal, for example, defining a differential pair. Selected suspended components 102 provide column-to-column termination including one signal to a reference voltage plane, such as a memory termination to reference voltage Vref. The suspended components 102 advantageously are easily arranged for electrical connection within grid array packages 100 to provide enhanced electrical performance.

Figure 2:
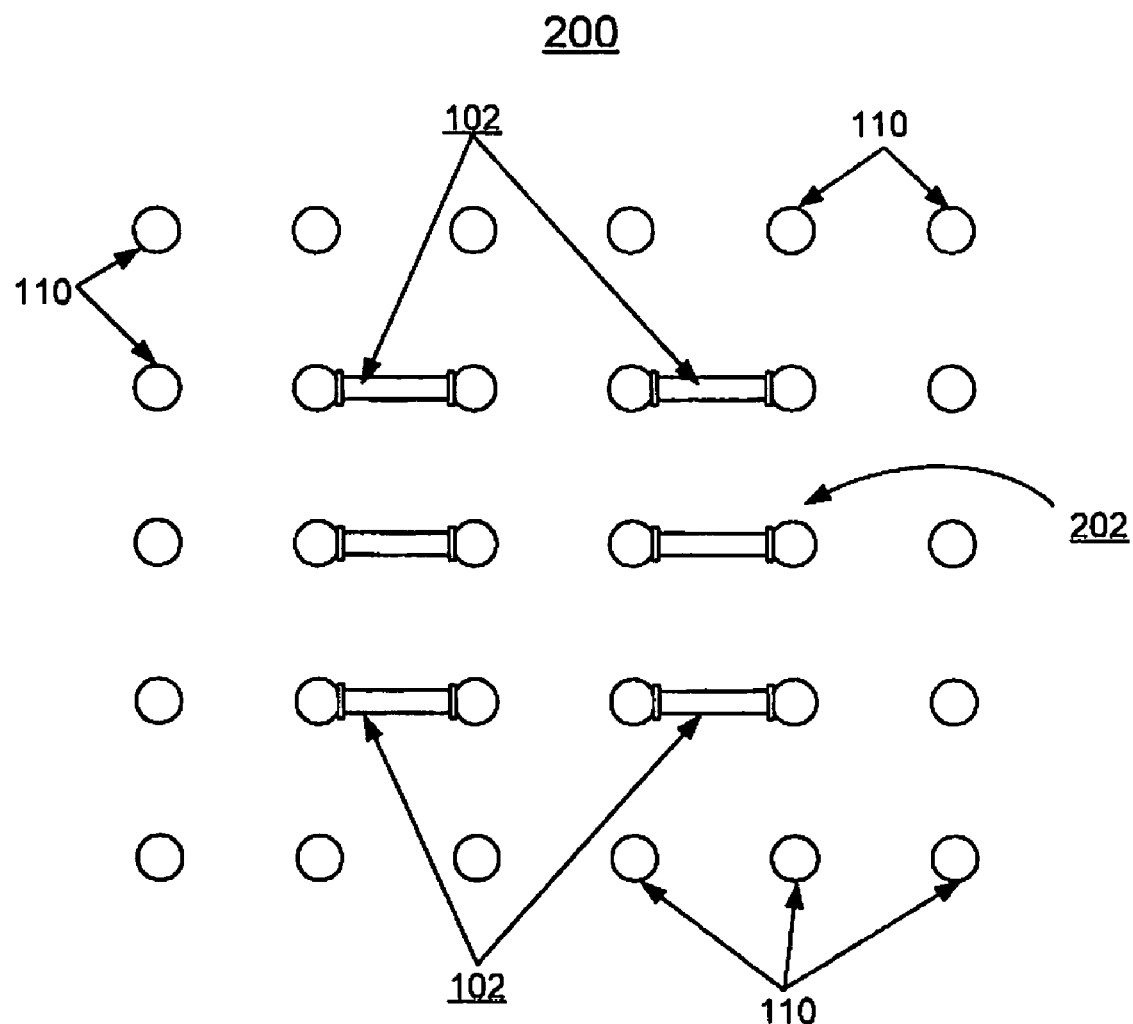
FIG. 2 is a top plan view not to scale illustrating an exemplary column grid array with incorporated suspended components of the electrical package assembly of FIG. 1 in accordance with the preferred embodiment.

Referring now to FIG. 2, there is shown not to scale an exemplary column grid array portion generally designated by the reference character 200, for example, of the solder column grid array 104 shown in FIG. 1. As shown in FIG. 2, a plurality of the suspended components 102 is generally located near a center portion generally designated by the reference character 202 of the column grid array 104. Such generally central placement of the suspended components 102 within the solder column grid array 104 enables improved reliability of the column grid array connection with the suspended components 102.

Figure 3:
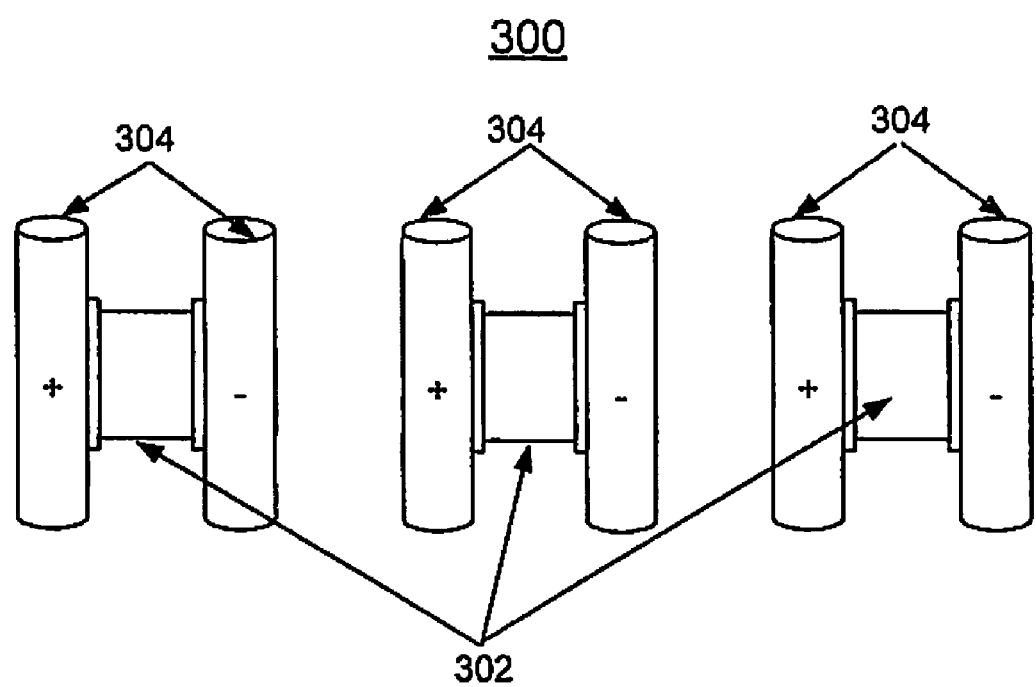
FIG. 3 is a side view not to scale illustrating an exemplary column grid array with incorporated suspended decoupling capacitors, for example, of the electrical pin grid array package assembly of FIG. 1 in accordance with the preferred embodiment.

Referring now to FIG. 3, there is shown not to scale another exemplary column grid array portion generally designated by the reference character 300, for example, of the solder column grid array 104. Column grid array portion includes a plurality of components 302, each connected between an adjacent pair of columns 304 within the solder column grid array 104. As shown, one of the pair of columns 304 is labeled + and the other is labeled − representing a column-to-column termination of a decoupling capacitor 302 including connection between power and ground for enhanced power decoupling.

Figure 4A:
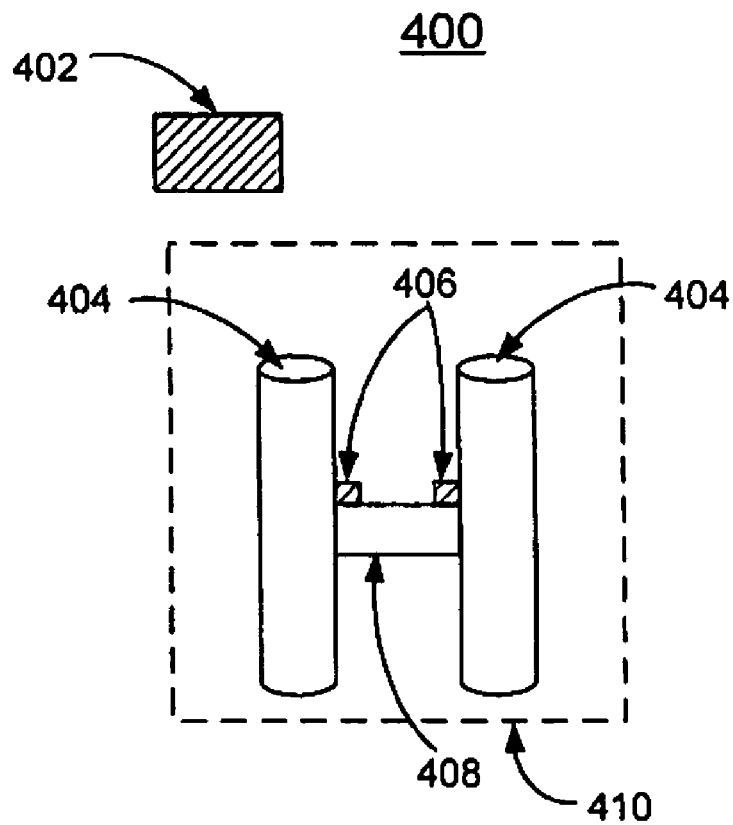
FIGS. 4A and 4B are respective side views not to scale illustrating processing steps of an exemplary portion of a column grid array with an incorporated suspended component for fabricating a column grid array with incorporated suspended components, for example, of the electrical pin grid array package assembly of FIG. 1 in accordance with the preferred embodiment.
Figure 4B:
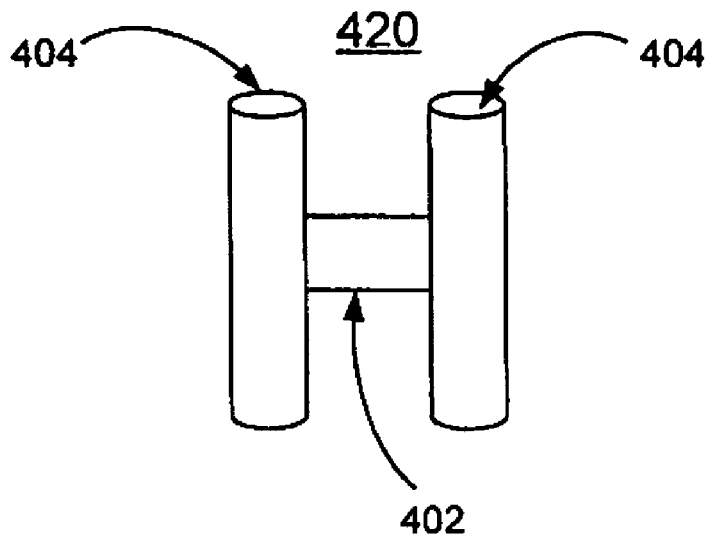

FIGS. 4A and 4B respectively illustrate exemplary processing steps of an exemplary portion of a column grid array with an incorporated suspended component for fabricating a column grid array with incorporated suspended components in accordance with the preferred embodiment.

Referring now to FIG. 4A, there is shown an initial structure of a first processing step generally designated by the reference character 400 including a component 402 to be positioned between a pair of columns or pins 404. A braze or solder, such as a high temperature solder 406 is applied to a portion 408 of a fixture 410. The component 402 is placed in the fixture 410 of FIG. 4A and the fixture portion 408 holds the component 402 in place. as shown in FIG. 4B.

Referring now to FIG. 4B, after the component 402 is placed in fixture 410, then in a next processing step heat is applied to form a resulting structure generally designated by the reference character 420. The structure or subassembly 420 includes the component 402 suspended between the pair of columns 404.

Figure 5:
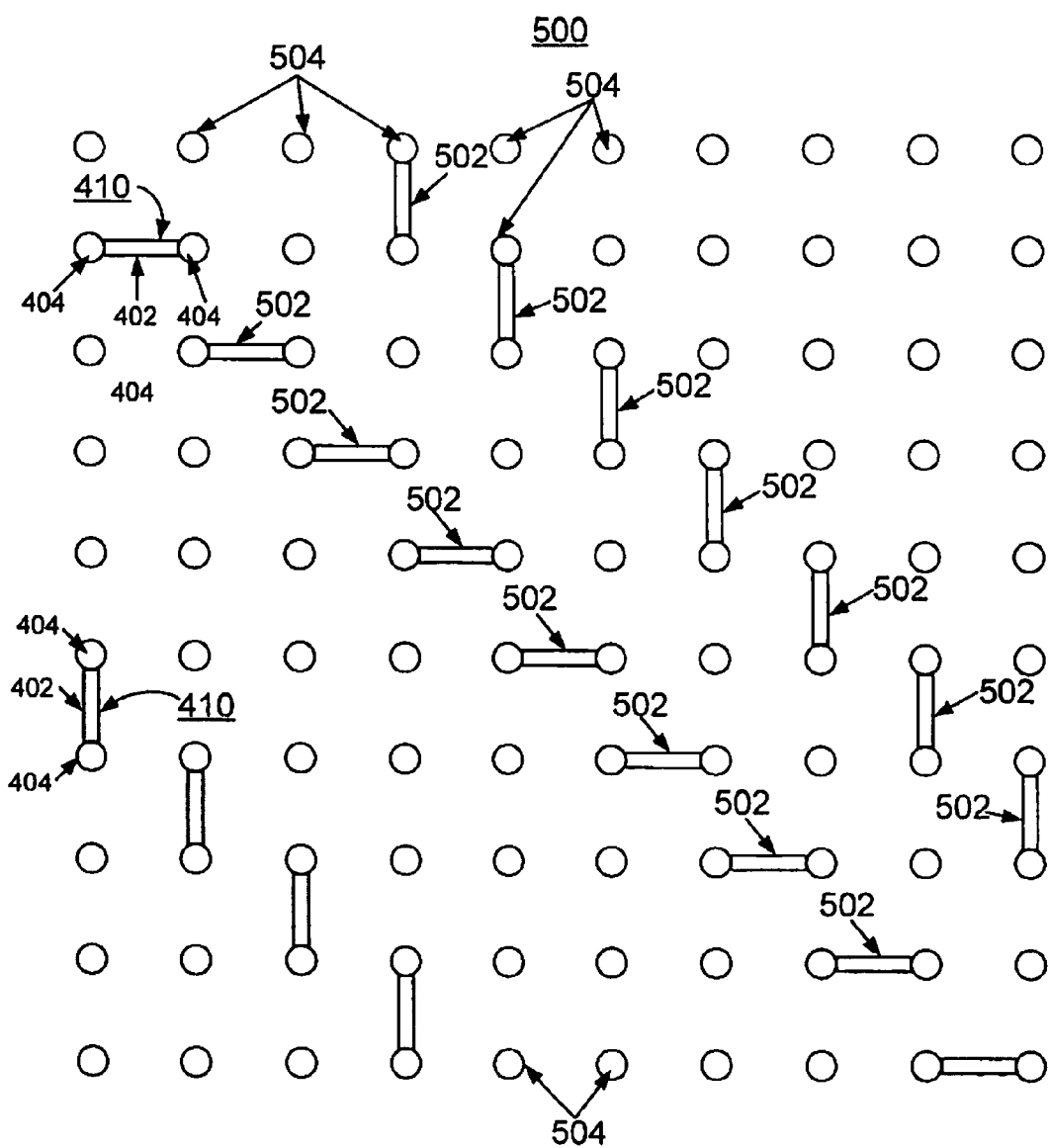
FIG. 5 is a top plan view not to scale illustrating another exemplary column grid array with incorporated suspended components, for example, of the electrical pin grid array package assembly of FIG. 1 in accordance with the preferred embodiment.

FIG. 5 illustrates another exemplary column grid array generally designated by the reference character 500 with incorporated suspended components in accordance with the preferred embodiment. As shown, the column grid array 500 includes a pair of the subassemblies 410, each including a respective component 402 connected between the pair of columns 404. Each subassembly 410 can be inserted into a predefined opening within the column grid array 500. Then the column grid array 500 including each installed subassembly 410 is heated to be cured or reflowed for attachment, for example, to the PCB 108 of the electrical pin grid array package assembly 100 of FIG. 1.

Alternatively, a conventional column attach fixture (not shown) can be used to hold the columns illustrated within the column grid array 500 prior to attach to the substrate. The conventional column attach fixture is modified to receive components 502 between selected columns 504, as shown in FIG. 5. This modification simply incorporates slots or reliefs in the fixtures to accommodate the selected components 502, including for example, decoupling capacitors and resistors, located between the columns or pins 504. A pre-application of solder or a braze paste or conductive adhesive is provided for the components 502. Then the components 502 are placed in the fixture to be cured or reflowed in the course of attachment to the printed circuit board or substrate.

While the present invention has been described with reference to the details of the embodiments of the invention shown in the drawing, these details are not intended to limit the scope of the invention as claimed in the appended claims.

What is claimed is:

1. A method for implementing component placement suspended within electrical pin grid array packages comprising:
   providing a column grid array between a printed circuit board and a first level package; said column grid array including a plurality of columns; and
   connecting a component between a predefined pair of said columns in the column grid array suspended between the printed circuit board and the first level package including applying solder to the component.

2. A method for implementing component placement suspended within electrical pin grid array packages as recited in claim 1 wherein the component includes a capacitor; and wherein connecting the component between a predefined pair of said columns includes providing column-to-column termination of the capacitor including connection between power and ground for enhanced power decoupling.

3. A method for implementing component placement suspended within electrical pin grid array packages as recited in claim 1 further includes heating the component and said predefined pair of said columns to form a subassembly.

4. A method for implementing component placement suspended within electrical pin grid array packages as recited in claim 3 further includes installing said subassembly within said column grid array.

5. A method for implementing component placement suspended within electrical pin grid array packages as recited in claim 1 further includes installing the component within said column grid array.

6. A method for implementing component placement suspended within electrical pin grid array packages as recited in claim 1 further includes heating the component and said column grid array to attach said column grid array to said printed circuit board and first level package.

7. A method for implementing component placement suspended within electrical pin grid array packages as recited in claim 1 further includes using of a slotted fixture to hold the component between said predefined pair of said columns.

* * * * *